United States Patent
Branch et al.

(10) Patent No.: US 11,510,631 B2
(45) Date of Patent: Nov. 29, 2022

(54) JOINT TEST DATA VISUALIZATION

(71) Applicant: RoboDiagnostics LLC, Atlanta, GA (US)

(72) Inventors: Thomas P. Branch, Atlanta, GA (US); Shaun K. Stinton, Chamblee, GA (US)

(73) Assignee: RoboDiagnostics LLC, Atlanta, GA (US)

( * ) Notice: Subject to any disclaimer, the term of this patent is extended or adjusted under 35 U.S.C. 154(b) by 305 days.

(21) Appl. No.: 16/818,106

(22) Filed: Mar. 13, 2020

(65) Prior Publication Data

US 2020/0289064 A1 Sep. 17, 2020

Related U.S. Application Data

(60) Provisional application No. 62/817,887, filed on Mar. 13, 2019.

(51) Int. Cl.
| | | |
|---|---|---|
| *G06T 13/40* | (2011.01) | |
| *A61B 5/00* | (2006.01) | |
| *A61B 5/11* | (2006.01) | |
| *G06T 19/20* | (2011.01) | |

(52) U.S. Cl.
CPC ........... *A61B 5/743* (2013.01); *A61B 5/1122* (2013.01); *A61B 5/4585* (2013.01); *A61B 5/7445* (2013.01); *G06T 13/40* (2013.01); *G06T 19/20* (2013.01); *A61B 2562/0252* (2013.01); *G06T 2210/41* (2013.01); *G06T 2219/2016* (2013.01)

(58) Field of Classification Search
None
See application file for complete search history.

(56) References Cited

U.S. PATENT DOCUMENTS

| | | |
|---|---|---|
| 2007/0055176 A1 | 3/2007 | Branch et al. |
| 2009/0124936 A1 | 5/2009 | Branch et al. |
| 2012/0046540 A1 | 2/2012 | Branch |
| 2014/0081181 A1 | 3/2014 | Branch |
| 2017/0143250 A1 | 5/2017 | Branch |
| 2017/0347945 A1 | 12/2017 | Branch |

OTHER PUBLICATIONS

Baillot et al., "Automatic Modeling of Knee Joint Motion for the Virtual Reality Dynamic Anatomy (VRDA) tool", Studies in Health and Technology and Informatics, 1999. (Year: 1999).*

(Continued)

*Primary Examiner* — Nicholas R Wilson
(74) *Attorney, Agent, or Firm* — Lempia Summerfield Katz LLC

(57) ABSTRACT

A method of evaluating a joint includes obtaining test data indicative of movement of the joint during a test of the joint, generating visualization data for a three-dimensional representation of the joint to be rendered via a display, generating plane data for a representation of a plane to be rendered via the display with the three-dimensional representation of the joint, the plane having a position and an orientation fixed relative to a bone of the joint, adjusting the visualization data to animate the three-dimensional representation to depict, via the display, the movement of the joint during the test, and adjusting the plane data to update the position and the orientation of the plane in accordance with the movement of the joint.

23 Claims, 6 Drawing Sheets

(56) References Cited

OTHER PUBLICATIONS

Thomas Proll, "Data Acquisition and Motion Interpolation for a Multimodal Medical Training Environment", 2006. (Year: 2006).*

Chae et al., "Change of gait after unilateral vestibular neuritis: a prospective longitudinal observation study", Scientific Reports, Nature, 2021, 9 pages.

Loredo et al., "Influence of High Heels On Walking Motion: Gait Analysis", Journal of Applied Biomechanics, Dec. 2015, 6 pages.

* cited by examiner

JOINT TEST DATA VISUALIZATION

CROSS-REFERENCE TO RELATED APPLICATION

This application claims the benefit of U.S. provisional application entitled "Joint Test Data Visualization," filed Mar. 13, 2019, and assigned Ser. No. 62/817,887, the entire disclosure of which is hereby expressly incorporated by reference.

BACKGROUND OF THE DISCLOSURE

Field of the Disclosure

The disclosure relates to joint testing.

Brief Description of Related Technology

Knee injuries and ligament damage have been diagnosed using the Dial test (or internal-external rotation test), the Lachman test (or anterior-posterior drawer test), and the Varus-Valgus test. When performed manually by individual medical personnel, these tests are limited by the specific clinician's subjective evaluation. The subjective nature of the tests may hinder the precision or accuracy of the diagnosis.

Others have attempted to reduce the manual nature of such joint testing by applying an instrument to the knee joint during testing. Several devices have been developed in attempts to more accurately quantify the extent of injury or relative displacement and compliance of a ligament in the knee. For example, Medmetric Corp has developed the KT-1000 and KT-2000 devices for measurement of the anterior-posterior translation of the tibia with respect to the femur.

The data generated by such joint testing has been presented via load-deformation curves. A load-deformation curve plots movement of the joint as a function of the torque or force applied to the joint. Each load-deformation curve presents the movement for a respective degree of freedom.

Unfortunately, some physicians and other individuals may find the load-deformation curves difficult to interpret. The challenge is increased by the possibility that the movement arising from the applied force may reside in six degrees of freedom of movement—i.e., translation along three axes, rotation about the three axes. As a result, characterizing the condition of a joint may call for evaluation of multiple load-deformation curves.

SUMMARY OF THE DISCLOSURE

In accordance with one aspect of the disclosure, a method of evaluating a joint includes obtaining, by a processor, test data indicative of movement of the joint during a test of the joint, generating, by the processor, visualization data for a three-dimensional representation of the joint to be rendered via a display, generating, by the processor, plane data for a representation of a plane to be rendered via the display with the three-dimensional representation of the joint, the plane having a position and an orientation fixed relative to a bone of the joint, adjusting, by the processor, the visualization data to animate the three-dimensional representation to depict, via the display, the movement of the joint during the test, and adjusting, by the processor, the plane data to update the position and the orientation of the plane in accordance with the movement of the joint In accordance with another aspect of the disclosure, a method of evaluating a joint includes obtaining, by a processor, test data indicative of movement of a mobile bone of the joint relative to a stationary bone of the joint during a test of the joint in which the mobile bone moves relative to the stationary bone, generating, by the processor, visualization data for a three-dimensional representation of the joint to be rendered via a display, generating, by the processor, plot data for a graphical representation of the test data to be rendered via the display, the graphical representation including a plot and an indicator disposed at a position along the plot, adjusting, by the processor, the visualization data to update the three-dimensional representation to depict, via the display, a playback of the movement of the mobile bone relative to the stationary bone during the test, and adjusting, by the processor, the plot data to update the position of the indicator during the playback such that the position of the indicator is representative of a current position of the mobile bone as depicted via the three-dimensional representation.

In accordance with yet another aspect of the disclosure, a system for evaluation of a joint includes a memory in which modeling instructions, graphical plot instructions, and data processing instructions are stored, and a processor coupled to the memory and configured through execution of the data processing instructions to obtain test data for a joint, the test data being indicative of movement of a mobile bone of the joint relative to a stationary bone of the joint during a test of the joint in which the mobile bone moves relative to the stationary bone. The processor is configured through execution of the modeling instructions to generate visualization data for a three-dimensional representation of the joint to be rendered via a display. The processor is further configured through the execution of the modeling instructions to generate plane data for a representation of a plane to be rendered via the display with the three-dimensional representation of the joint, the plane having a position and an orientation fixed relative to the mobile bone of the joint. The processor is further configured through the execution of the modeling instructions to adjust the visualization data to update the three-dimensional representation to depict, via the display, a playback of the movement of the mobile bone relative to the stationary bone during the test. The processor is further configured through the execution of the modeling instructions to adjust the plane data to update the representation of the plane in accordance with the movement of the joint.

In connection with any one of the aforementioned aspects, the systems, devices, and/or methods described herein may alternatively or additionally include any combination of one or more of the following aspects or features. Adjusting the plane data modifies a characteristic of the plane when the movement falls outside of a normative range of motion for the joint. The method further includes adjusting, by the processor in response to a user input, the plane data to change the position of the plane relative to the bone. The plane is a first plane of a plurality of planes. The method further includes generating, by the processor, further plane data for a representation of a second plane of the plurality of planes, the second plane having a position and an orientation fixed relative to a second bone of the joint, and modifying, by the processor, a characteristic of the second plane when the first plane and the second plane intersect. The second bone is a stationary bone of the joint. The method further includes modifying, by the processor, a characteristic of the three-dimensional representation when the movement falls outside of a normative range of motion for the joint. Generating the three-dimensional representation includes customizing the three-dimensional representation to modify a bone spacing of the joint. Generating the three-dimensional representation of the joint includes receiving a user input directed to modification of the three-dimensional representation, and modifying a zoom level and/or a viewing perspective of the three-dimensional representation in response to the user input. Adjusting the three-dimensional representation includes receiving a user input directed to controlling playback of the movement of the joint during the test. Adjusting the three-dimensional representation includes depicting the movement in scale relative to dimensions of the joint. Obtaining the test data includes capturing the test data via a robotic test apparatus. The method further includes rendering, by the processor, on the display, the adjusted three-dimensional representation of the joint and the representation of the plane with the updated position and the updated orientation of the plane to depict the movement of the joint. The method further comprising rendering, by the processor, on the display, a depiction of normative motion of the joint while rendering the three-dimensional representation of the test data. The method further includes generating, by the processor, plane data for a representation of a plane to be rendered via the display with the three-dimensional representation of the joint, the plane having a position and an orientation fixed relative to the mobile bone of the joint, and adjusting, by the processor, the plane data to update the position and the orientation of the plane in accordance with the movement of the joint. Adjusting the plane data modifies a characteristic of the plane when the movement falls outside of a normative range of motion for the joint. The method further includes adjusting, by the processor in response to a user input, the plane data to change the position of the plane relative to the bone. The plane is a first plane of a plurality of planes. The method further includes generating, by the processor, further plane data for a representation of a second plane of the plurality of planes, the second plane having a position and an orientation fixed relative to a stationary bone of the joint, and modifying, by the processor, a characteristic of the second plane when the first plane and the second plane intersect. The graphical representation comprises a load-deformation curve. The graphical representation depicts the movement in a secondary degree of freedom other than a primary degree of freedom in which a force is applied to the joint to cause the movement. The method further includes adding, by the processor, a depiction of normative motion of the joint to the graphical representation of the test data.

BRIEF DESCRIPTION OF THE DRAWING FIGURES

For a more complete understanding of the disclosure, reference should be made to the following detailed description and accompanying drawing figures, in which like reference numerals identify like elements in the figures.

Figure 1:
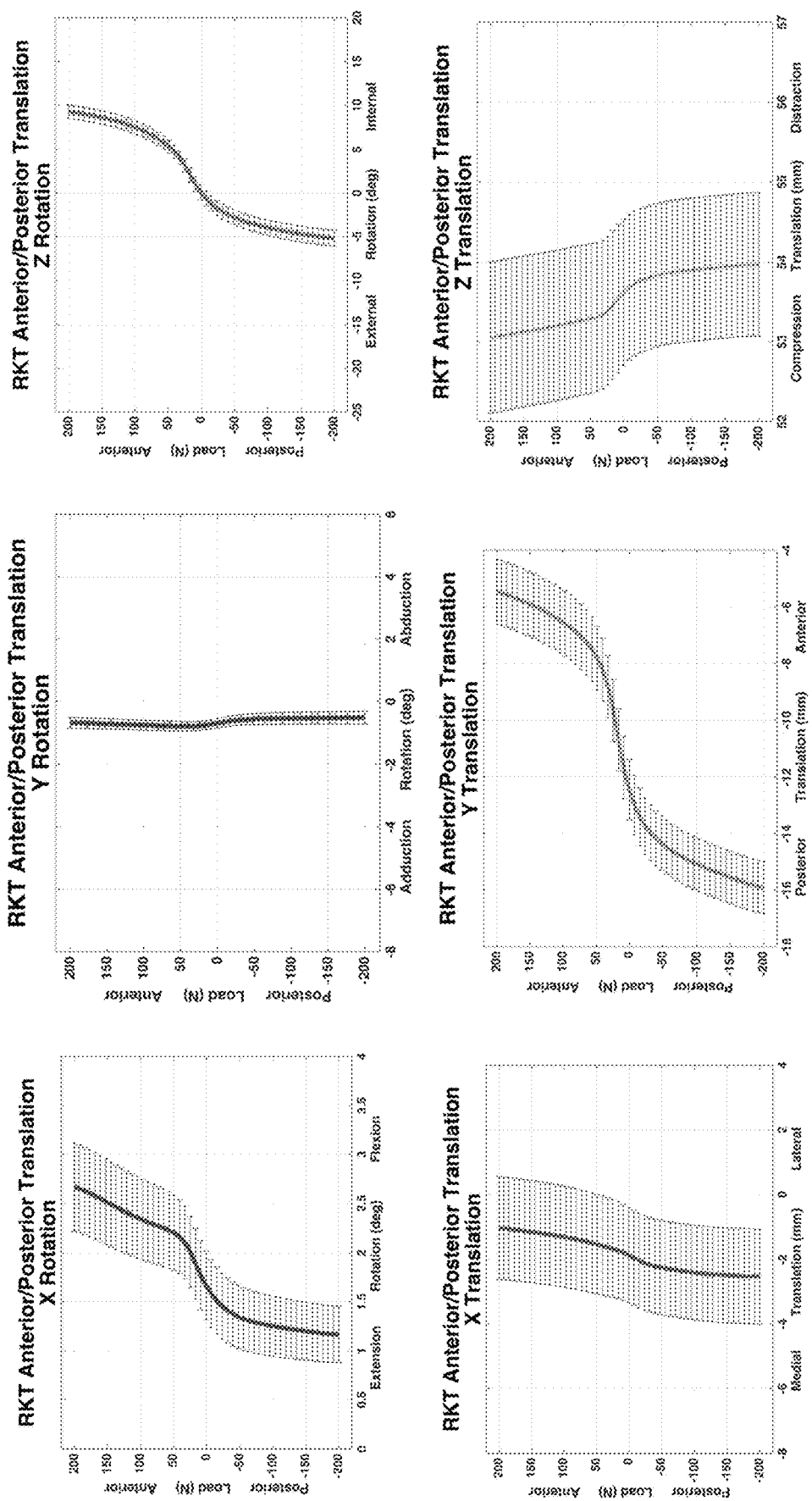
FIG. 1 depicts examples of load-deformation curves indicative of test data generated by a joint test apparatus during a test in which a torque is applied to drive movement in an anterior/posterior direction.

The embodiments of the disclosed apparatus, devices, and methods may assume various forms. Specific embodiments are illustrated in the drawing and hereafter described with the understanding that the disclosure is intended to be illustrative. The disclosure is not intended to limit the invention to the specific embodiments described and illustrated herein.

DETAILED DESCRIPTION OF THE DISCLOSURE

Systems and methods for evaluating a joint are described. The systems and methods are useful in connection with joint testing and evaluation procedures in which a joint is manipulated via application of one or more torques or forces and the resulting movement is measured. Test data indicative of the measurements is then visualized via the systems and methods support the evaluation of the joint. The visualization may include both a three-dimensional representation of the joint and a graphical representation (e.g., a load-deformation curve) of the test data. The three-dimensional representation is updated to depict a playback of the movement of the joint during the test. The graphical representation includes an indicator on a plot of the test data. The position of the indicator is updated during the playback such that the indicator is representative of a current position of the joint (e.g., a mobile bone of the joint) as depicted via the three-dimensional representation. The three-dimensional and graphical representations of the test data are thereby correlated. The three-dimensional representation may help a physician or other user to interpret the graphical representation of the test data, and vice versa. In these and other ways, the disclosed systems and methods facilitate and improve the visualization, interpretation, and evaluation of the test data, as well as the evaluation of the joint.

The visualization provided by the disclosed systems and methods may be facilitated via the incorporation of one or more planes into the three-dimensional representation of the joint. Each plane has a position and an orientation fixed relative to a bone of the joint. In a knee example, two planes may be incorporated—one for the femur, and one for the tibia. The position and the orientation of the plane(s) is then updated in accordance with the movement of the joint. Each plane helps a user visualize the often small movements arising from the test. The movement in secondary degrees of freedom, i.e., those degrees of freedom other than that in which the force is applied, may be especially infinitesimal and otherwise indiscernible. The incorporation of the plane(s) allows the movement of the joint to be presented in scale with the three-dimensional representation of the joint, despite the sizes involved. The incorporation of the plane(s) avoids having to rely on amplification or exaggeration to assist in visualization of the movement. The test data is thus presented without introducing inaccuracies or distortions of the test data.

The disclosed systems and methods are configured to support the customization of the visualization of the test data. The customization may be directed to accommodating the preferences of a physician or other user. A physician may thus save one or more preferred views or perspectives for future use. The customization may alternatively or additionally be automatically implemented in accordance with the nature of the tests, the test data, and/or other factors. For example, the disclosed systems and methods may be configured to automatically present one or more specific views or perspectives for the three-dimensional representation(s) and a specific set of load-deformation curves for a given test.

Although described below in connection with knee testing, the disclosed systems and methods are well suited for use in evaluating a variety of other joints. For example, the disclosed systems and methods may be used to evaluate joints, such as elbow joints, shoulders, ankles, wrists, and the like. The disclosed systems and methods are also not limited to use in connection with any particular types of joint tests (e.g., the anterior-posterior translation test, the internal-external rotation test, and the varus-valgus test). The tests may accordingly vary from the examples described and referenced herein.

The test data used by the disclosed systems and methods may be captured with a joint testing apparatus, such as a robotic test apparatus, to provide a controlled application of torque during joint examination. The apparatus may control the magnitude, direction, and rate of torque application for one or more tests. The apparatus may be configured as described in U.S. Patent Publications Nos. 2012/0046540 ("Robotic Knee Testing Device, Subjective Patient Input Device, and Methods for Using Same"), 2014/0081181 ("Robotic Knee Testing (RKT) Device having Decoupled Drive Capability and Systems and Methods Providing the Same"), and 2017/0347945 ("Robotic Knee Testing Apparatus and Patient and Apparatus Set-Up Methods"), the entire disclosures of which are hereby incorporated herein by reference. Other apparatus may be used.

In each of the tests, the robotic test apparatus is configured to drive movement of a mobile bone of the joint relative to a stationary bone of the joint. The playback of the joint movement may thus depict movement of the mobile bone relative to the stationary bone. In knee examples, the femur is the stationary bone, and the tibia is the mobile bone. The mobile bone may be directly or indirectly driven by the robotic test apparatus. The stationary bone may be clamped or otherwise fixed in place. In some cases, the stationary bone may exhibit a small amount of residual movement during the testing, but nonetheless be effectively stationary due to either the de minimus nature of the residual movement and/or compensation therefor. The stationary bone may thus be nevertheless considered stationary in such circumstances.

The representations rendered by the disclosed systems and methods may be integrated with other user interfaces and systems. For example, the representations may be provided in connection with an electronic medical record (EMR). The underlying data may be uploaded or otherwise added to the record of a patient. The user interface for the electronic medical record may then include one or more user interfaces through which the visualization of the data may be accessed. The user interface may also be configured and used to obtain feedback or other information from the patient and/or other individuals regarding the condition of the joint. The system may be configured to facilitate gathering of the feedback. For example, the system may send a reminder or other message to the patient that a survey or questionnaire is due or available.

The visualization of the movement via three-dimensional representation may be used to illuminate the data provided by one or more graphical representations of the test data. In some cases, the graphical representations may be load-deformation curves. Other graphical representations may be used, including, for instance, graphical representations that depict the movement in one degree of freedom versus time or another degree of freedom. A number of graphical representations may be used to depict the movement. For example, six load-deformation curves may be generated for a respective test, one for each degree of freedom—translation along the three axes and rotation about the three axes.

FIG. 1 depicts an example of the six load-deformation curves for an anterior-posterior translation test on a knee joint. Although the force is applied to the knee in the anterior-posterior direction, the resulting movement of the tibia includes motion in all six of the degrees of freedom. Although the six plots fully characterize the resulting movement, it may difficult for some individuals to evaluate the knee under test based solely on the plots. The disclosed systems and methods provide a way of visualizing the same data presented via the plots to facilitate the evaluation. As described below, the visualization techniques of the disclosed systems and methods may supplement the load-deformation plots with one or more three-dimensional representations of the movement. The three-dimensional representations may be selected and/or otherwise tailored to suit the individual preferences of a surgeon or other individual. For example, the joint may be viewed from a perspective from which the surgeon is accustomed. The disclosed systems and methods may also present one or more of the graphical representations in a manner correlated with the three-dimensional representation such that playback of the movement is depicted via both the graphical and three-dimensional representations.

Figure 2:
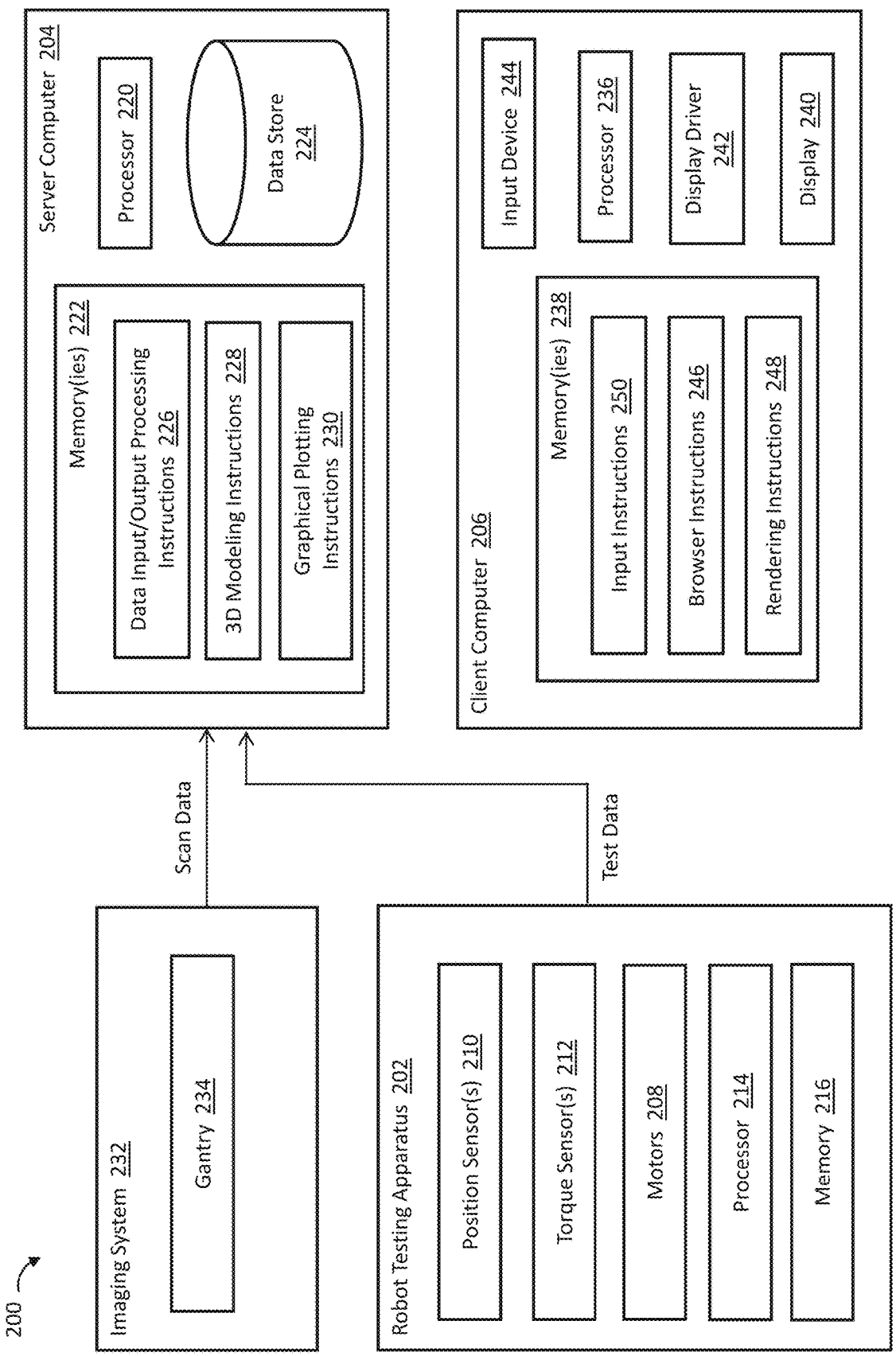
FIG. 2 is a block diagram of a system for evaluation of joint test data in accordance with one example.

FIG. 2 illustrates a system 200 directed to evaluating a joint through three-dimensional and other representations of test data. The system 200 is directed to processing the test data so that the test data is visualized or presented in a manner that facilitates the evaluation thereof. The system 200 includes a robot testing apparatus 202 to capture the test data. The system 200 includes one or more computer devices or systems to process the test data and support the visualization of the joint movement. In this example, the system 200 includes a server computer 204 and a client computer 206. The server computer 204 may be or include one or more networked computing devices, including, for instance, server computing devices disposed in a cloud arrangement. The client computer 206 may be or include a workstation, terminal computer, desktop computer, portable computer, handheld device, or other computing device. Other distributed or non-distributed computing architectures may be used. For instance, the system 200 may include a single computer device to process the test data and render the visualization and other representations of the joint movement. The assignment and handling of the computing tasks described herein may thus vary considerably from the example shown.

The robot testing apparatus 202 is configured to implement joint testing, such as rotational joint testing and translational joint testing of a joint. For example, the rotational joint testing may be or include internal-external rotation and/or varus-valgus rotation of a knee or other joint. The translational joint testing may be or include anterior-posterior translation of the knee or other joint. The robot testing apparatus 202 implements the rotational and translational joint testing to acquire or capture test data indicative of rotational and translational movement of the joint during the rotational and translational joint testing, respectively. For instance, in implementing such testing, the robot testing apparatus 202 may be configured to detect position and force (e.g., torque) data while a force (e.g., torque) is applied to the joint. The position data may be processed to determine translational displacements along three orthogonal axes of a coordinate system that define or correspond with three degrees of freedom for the joint, as well as orientations (e.g., rotational displacements) about those three axes that correspond with the other three degrees of freedom for the joint. A range of rotational or translational motion may then be determined for the joint in each degree of freedom.

The robot testing apparatus 202 includes a number of motors 208, one or more position sensors 210 directed to capturing position data, and one or more torque sensors 212 directed to capturing torque data. The motors 208, the position sensor(s) 210, and the torque sensor(s) 212 may be configured as described in the above-referenced patent publications or otherwise configured. The torque sensors 212 may be used to detect the torque applied by the respective motor 208 or measure a reactive force resulting from the application of the torque. These components of the robot testing apparatus 202 may vary from the example shown. For instance, each torque sensor 212 may be an integrated torque transducer of a respective one of the motors 208. In some cases, the torque may be measured by measuring a current level of the motor 208.

The robot testing apparatus 202 implements the joint testing by imparting or applying one or more forces to the joint. The motors 208 of the robot testing apparatus 202 may be configured such that each force is oriented in a respective plane or degree of freedom for the joint. In examples described in the above-referenced publications in which the joint is a knee, the joint testing may include a respective torque applied to cause external-internal rotational movement, varus-valgus rotational movement, and/or anterior-posterior translational movement. The anterior-posterior translational movement may be driven by torque applied by one of the motors 208. Additional and/or alternative joint tests may be implemented. The number and types of the joint tests implemented by the robot testing apparatus 202 may thus vary accordingly.

The robotic testing apparatus 202 is configured to capture data indicative of the motion of the joint during the joint testing. The data may be raw sensor data generated by the position sensors 210 and the torque sensors 212 and/or processed data derived from the raw data. Either way, to acquire the data, the robotic testing apparatus 202 may apply a range of forces (e.g., torque levels) to the joint under test. The sensors 210, 212 capture the position and torque data during the resulting joint movement. For example, the position and torque data from each sensor 210, 212 may be sampled at a particular rate. The position and torque data may then be processed (e.g., interpolated) to generate test data at specific intervals, such as specific torque levels.

The torque sensors 212 may provide torque data regardless of whether the motor 208 with which the torque sensor 212 is associated is applying force to the joint. The torque sensor 212 for an inactive one of the motors 208 may thus provide data indicative of the reactive force resulting from the torque applied in another plane or degree of freedom. The reactive force is indicative of the force applied by the joint on the torque sensor 212 of the inactive motor 208. The measured reactive forces may thus be referred to as secondary, concomitant, or incidental forces or torques.

The processing of the raw data may include generating data indicative of an extent, displacement, or range of motion in one or more degrees of freedom for the joint. For instance, the respective extent or range of motion may be determined for the primary movement and/or one or more secondary movements resulting from the application of a range of force (e.g., torque) levels.

The processing of the raw data may also include combining the position and force (or torque) data to generate load-deformation data for the joint under test. The load-deformation data for the joint may include a set of force-position data points over the range of forces. The load data in each data set may be representative of the applied force (or torque) or the resulting reactive force (or torque) measured in one of the other degrees of freedom.

The processing of the raw data and/or other test data may be implemented by the robot testing apparatus 202, the server computer 204, the client computer 206, and/or another computer. In the example of FIG. 2, the test data (e.g., the raw data) is provided to the server computer 204 for at least some of such processing. Alternatively or additionally, some or all of the processing is implemented by a processor 214 of the robot testing apparatus 202. The processor 214 implements data processing instructions stored on a memory 216. The processor 214 and the memory 216 may be provided or realized as a computer or other device connected to, or otherwise in communication with, the sensors 210, 212. The device may be or include a specialized computing device dedicated to controlling the robot testing apparatus 202, such as a programmable logic controller (PLC), and/or a general purpose computer programmed via the instructions in the memory 216.

The extent to which the raw data is processed prior to delivery to the server computer 204 may vary. For instance, in some cases, the data provided to the server computer 204 may or may not correspond with the data provided by the sensors 210, 212. In other cases, the data provided by robot testing apparatus 202 is or includes load-deformation data. The load-deformation data may include the position data for any one of the six degrees of freedom as a function of the torque or force data measured by any one of the torque sensors 210.

The server computer 204 includes a processor 220 and a memory 222 for processing the test data captured by the robot testing apparatus 202 and/or the load-deformation data derived therefrom. The processor 220 is coupled to, or otherwise in communication with, the robot testing apparatus 202. In this example, the server computer 204 also includes a data store 224 in which data is stored for use in connection with the processing. The data store 224 may include a database in which test data and other patient data is stored. That test data and/or another data structure stored in the data store 224 may include normative data representative of motion of one or more healthy joints. The data store 224 may also include data indicative of a three-dimensional model of the joint. Such model data may be used to generate the three-dimensional representation of the joint movement. The model data may be useful when generic bones of the joint are sufficient for the visualization.

The processor 220 is coupled to the memory 222 to access instructions and/or other data stored on the memory 222. In the example of FIG. 2, data input/output processing instructions 226, three-dimensional modeling instructions 228, and graphical plotting instructions 230 are stored on the memory 222. The instructions 226, 228, 230 may be stored as one or more modules or instruction sets, and may be integrated to any desired extent. The memory 222 may have additional data stored thereon, such as load-deformation data for the joint under test or other joint instances. The memory 222 may be or include any number of memories, storage devices, and/or other computer-readable media.

The processor 220 is configured through execution of the data processing instructions 226 to obtain and/or process test data for a joint. As described above, the test data is indicative of motion of the joint during the joint testing implemented by the robotic testing apparatus 202. The test data may be obtained by conducting one or more joint tests. Raw sensor data may be obtained for one or more tests. In some cases, the data processing instructions 226 cause the processor 220 to request the raw sensor or other test data from the robot testing apparatus 202. Alternatively or additionally, the processor 220 accesses a memory to obtain the test data. In other cases, the data may be received (e.g., provided) without a request. For instance the input instructions 222 may cause the processor 220 to access the memory 222, the data store 224 and/or another memory or data store, to obtain the test data, e.g., from previously implemented joint testing.

The test data may thus be obtained in additional and/or alternative ways. For instance, the processor 220 may be configured to obtain the underlying raw sensor data from the robot testing apparatus 202 for the joint testing. In some cases, the test data obtained from the robot testing apparatus 202 may be or include processed data. The test data, whether raw or processed, and/or other data indicative of the joint movement, may be stored in the memory 222, the data store 224, and/or another memory or data store.

The processor 220 is configured through execution of the data processing instructions 226 to generate test or other data indicative of the movement of the joint. The implementation of the data processing instructions 226 in connection with knee joint examples may involve processing the test data from an anterior-posterior translation test, an external-internal rotation test, a varus-valgus test, or a test involving a combination of the motion in such tests, and/or one or more alternative or additional tests. The processing of the test data in accordance with the data processing instructions 226 (and/or other instructions) may include various calculations. The calculations may be in support of and/or in addition to the calculations directed to generating one or more load-deformation curves. For example, the processing may include one or more coordinate system transformations and/or other kinematic processing. In some knee joint examples, the transformations include transforming (1) the femur orientation from an anatomical space (defined, e.g., via anatomical markers) to a world coordinate system of the robot testing apparatus 202, (2) the tibia orientation from an anatomical space to the world coordinate system, (3) the femur orientation from the world coordinate system to a sensor coordinate system (e.g., a femur or tibia sensor), (4) the tibia orientation from the world coordinate system to a sensor coordinate system, and (5) the tibia orientation from the world coordinate system to a femur coordinate system. Further transformations may be used to account for the origins of the coordinate systems. Collectively, these transformations may be directed to producing data indicative of the motion of the joint from a particular perspective. For instance, in some knee joint examples, the data is indicative of the motion of the tibia in the coordinate system of the femur. The extent to, and manner in, which the sensor data provided to the processor 220 is processed via the input instructions 226 may vary. For instance, the sensor data may be normalized or interpolated to any desired extent.

Figure 4:
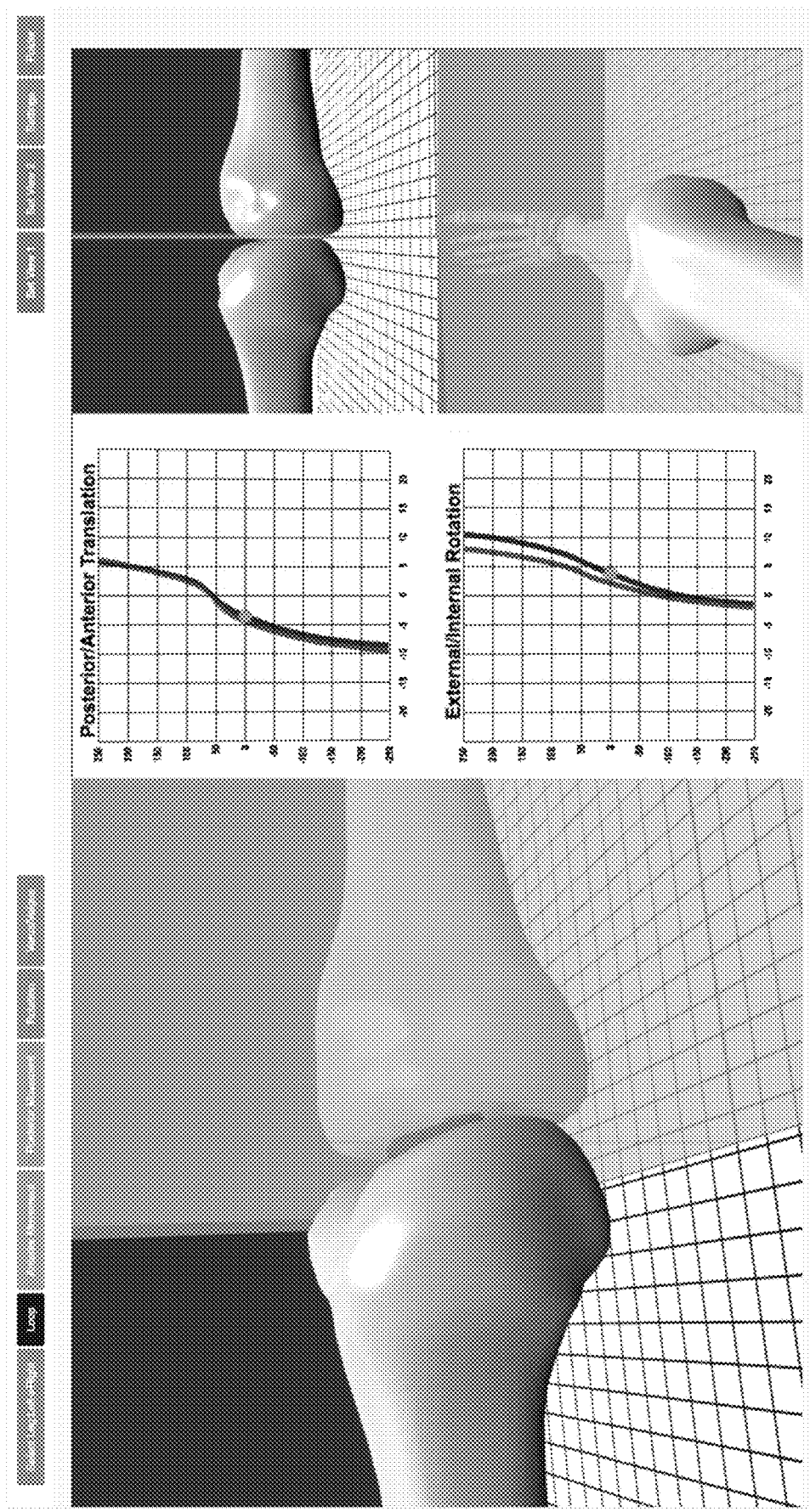
FIG. 4 is an example of a user interface display generated by the system of FIG. 2, in accordance with the method of FIG. 3, or by or in accordance with another system or method, in which an animated three-dimensional representation of the joint is rendered along with a dynamic graphical representation of the test data.
Figure 5:
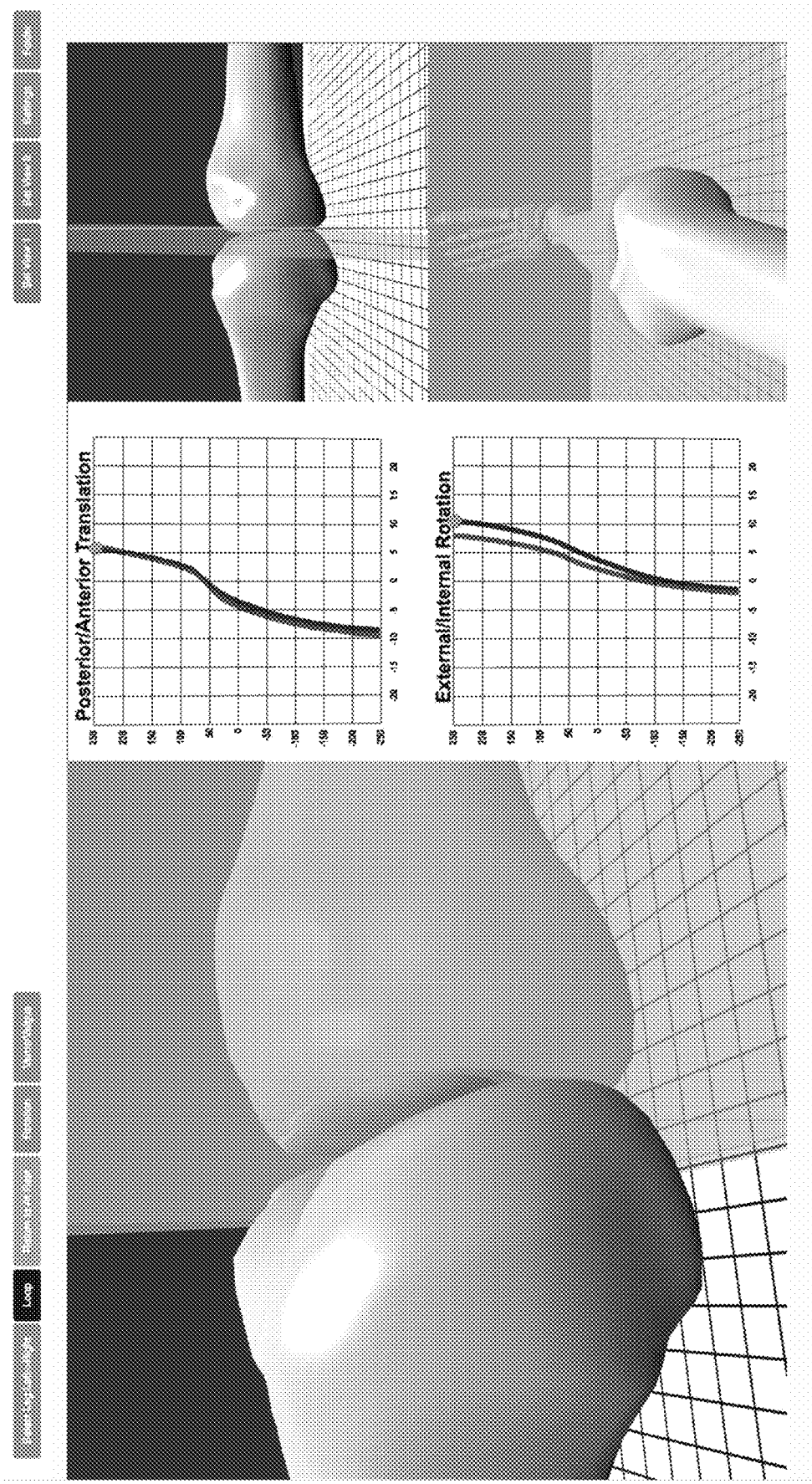
FIG. 5 shows the user interface display of FIG. 4 after updating of the three-dimensional representation to depict a playback of the movement of the joint during the test.

The processor 220 is configured through execution of the modeling instructions 228 to generate visualization data for one or more three-dimensional representations of the joint to be rendered via a display, such as a display of the client computer 206. In one example, multiple representations are generated and rendered to provide different perspectives or views of the joint. The model instructions 228 may cause the processor 220 to access the data store 224 to obtain model data for the joint. For instance, the model data may be representative of bones and other elements of the joint. In a knee example, the model data may be used to render a three-dimensional image of a femur, a tibia, and/or other bones involved or associated with the knee. Examples are shown in FIGS. 4 and 5.

The model data may be generic or otherwise not specific to the patient for which the test data was obtained. Alternatively, the data store 224 may include multiple models for a specific joint to address different patient circumstances. The modeling instructions 228 may then cause the processor 220 to customize the three-dimensional representation by selecting one or more of the available models or otherwise customizing the model data for the test data being visualized. For instance, the modeling instructions 228 may cause the processor 220 to customize the three-dimensional representation by incorporating scan data of the joint under test. The three-dimensional representation may thus be personalized to the patient, as opposed to using generic model data.

The system 200 may include an imaging system 232 to obtain the scan data. The scan data may be used to customize the rendering of the bones of the joint in the three-dimensional representation. The patient's own bones may thus be depicted rather than a model representation of the bones. The imaging system 232 may be or include a computed tomography (CT) scanner, magnetic resonance imaging (MRI) scanner, and/or other scanner or medical imaging device. The imaging system 232 may alternatively or additionally be used to obtain position data during the test(s). To that end, the robot testing apparatus 202 may be configured to allow the patient to be disposed within a gantry 234 of the imaging system 232 during the testing. Further details regarding the use of an imaging device to obtain the test data are set forth in the above-referenced publications.

The modeling instructions 228 may direct the processor 220 to customize or modify the three-dimensional representation in other ways. For example, a bone gap or other spacing may be modified. In knee cases, the gap between the femur and tibia may be modified from a default representation to account for patients that may have had, for instance, a meniscectomy. An individual with a meniscectomy will have less joint space than someone with a healthy meniscus. The gap between the bones at the default position may be changed to address other conditions of the individual subject's knee. The nature of the customization may thus vary.

The modeling instructions 228 may be configure the processor 220 to provide the three-dimensional representation(s) with various visualization options. For example, zoom level, rotation, and pan options may be provided. The viewer may accordingly adjust the three-dimensional representation to provide a desired perspective or view of the joint.

The modeling instructions 228 may also cause the processor 220 to incorporate one or more planes into the three-dimensional representations. In those cases, the processor 220 is further configured through the execution of the modeling instructions 228 to generate plane data for a representation of each plane to be rendered via the display with the three-dimensional representation of the joint. Each plane has a position and an orientation fixed relative to a bone of the joint. The plane moves with the bone movement. The orientation of the plane also changes as the bone reorients. The plane(s) may thus facilitate observation of the joint movement, which may be relatively small in scale. In this way, the depiction of the plane(s) allows the movement to be depicted in scale.

The depiction of the planes may facilitate other aspects of the three-dimensional representation of the movement. For instance, the color (or other characteristic) of the plane(s) may be modified to indicate a certain circumstance or condition. In some cases, the color of a plane may change from one color (e.g., green) to another color (e.g., red) when the plane intersects another plane. Alternatively or additionally, the color or other characteristic of a plane may be modified to indicate that the position of the bone has exceeded a range, such as a normative range. Other conditions or circumstances may be flagged via a change in the depiction of the plane(s). For example, the depiction of the plane may change if the speed of the moving bone passes a threshold value. An increase in speed that occurs suddenly may indicate slippage of the bone (e.g., a femur sliding off the tibia). The manner in which the normative range or other behavior is specified may vary. Data indicative of a normative range or behavior may be stored in the data store 224.

The modeling instructions 228 may direct the processor 220 to provide options for user customization of the plane(s). In some cases, the position of a plane relative to the bone to which it is fixed may be modified by a user. For example, the plane may be moved closer to, or farther from, the end of the bone.

Examples of planes in connection with a knee-based example are shown in FIGS. 4 and 5. In those examples, a first plane is positioned at the end of the femur, and a second plane is positioned at the end of the tibia. FIG. 4 depicts a starting position of the joint in which the two planes are oriented in parallel with one another. The initial orientation of each plane may be user-configurable or otherwise modified. Each plane extends outward from the bones, e.g., beyond the outer perimeter of the bones.

Figure 6:
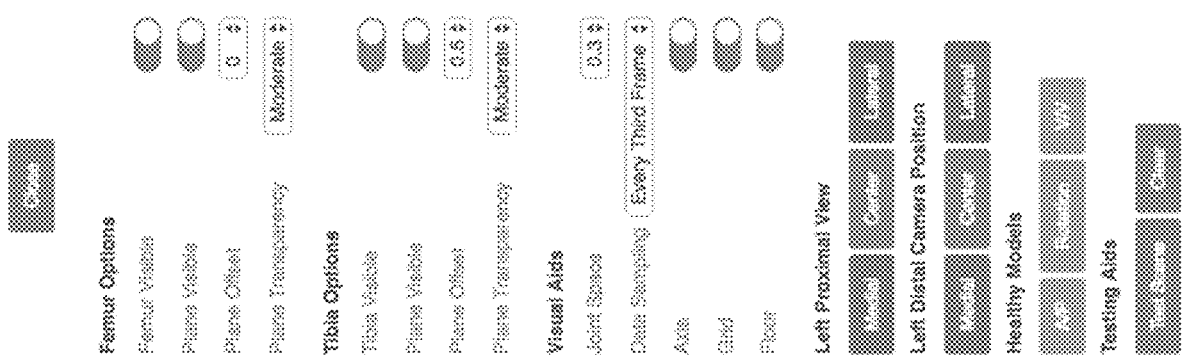
FIG. 6 is an example of a user interface display generated by the system of FIG. 2, in accordance with the method of FIG. 3, or by or in accordance with another system or method, to provide settings or options to configure the three-dimensional and graphical representations of the test data.

User settings may specify whether the plane(s) are visible, as well as various characteristics of the plane(s). For example, the transparency of the plane(s) may be selected. An example of an interface for the user settings is shown in FIG. 6.

The processor 220 is configured through execution of the graphical plot instructions 230 to generate plot data for a graphical representation of the test data to be rendered via the same display on which the three-dimensional representation is rendered. The graphical representation includes one or more plots. In some cases, the plot(s) may be or include load-deformation plots. Additional or alternative plots may be provided, including, for example, plots of joint movement in one degree of freedom relative to another degree of freedom. In each plot, an indicator, such as a dot or other marking, is disposed at a position along the plot. The indicator represents the current position along the load-deformation curve being shown in the three-dimensional representation(s).

The visualization data and the plot data is adjusted to provide a playback of the joint movement. The playback includes animating the three-dimensional representation(s) of the joint, while updating the graphical plot(s) of the joint movement. In the example of FIG. 2, the processor 220 is further configured through the execution of the modeling instructions 228 to adjust the visualization data to update the three-dimensional representation to depict, via the display, a playback of the movement of the joint during the test. The processor 220 is further configured through the execution of the graphical plot instructions 230 to adjust the plot data to update the position of the indicator during the playback such that the position of the indicator is representative of a current position of the joint (e.g., the mobile bone of the joint) as depicted via the three-dimensional representation. In examples in which one or more planes are depicted, the processor 220 is further configured through the execution of the modeling instructions 228 to adjust the plane data to update the representation of the plane in accordance with the movement of the joint.

The load-deformation data for a particular degree of freedom may be or include a load-deformation curve fitted to the load-deformation data. A variety of different curve fitting techniques or procedures may be used to generate a load-deformation curve for the load-deformation data. In some examples, regression modeling techniques, principal component analysis (PCA), or other techniques are used. In other cases, one or more quadratic curves are fitted to the load-deformation data. Other polynomial functions of varying order may alternatively be used. In still other cases, the test data is presented in graphical form without a curve fitting.

The example of FIG. 2 depicts a server-client architecture for providing the visualization of the test data. In that architecture, the generation of the visualization data and plot data and other data processing of the test data is implemented by the server computer 204 for display at the client computer 206. The client computer 206 includes a processor 236, a memory 238, a display 240, a display driver 242, and one or more input devices 244. Data exchanges between the server computer 204 and the client computer 206 may be implemented via an internet protocol. To that end, the client computer 206 may be configured to implement a browser application via execution of browser instructions 246 stored in the memory 238. A user interface via which the visualization of the test data is rendered may be generated within the browser application or provided separately therefrom. In some cases, rendering instructions 248 may be executed by the processor 236 to generate image or frame data for the display driver 242, which, in turn, sends pixel or other control signals to the display 240. The user interface may be configured to accept various user commands via the input device(s) 244 to customize or otherwise control the visualization of the test data.

Other computing architectures or arrangements may be used. For instance, the data processing and data display may be implemented on a single computing device. Alternatively, the data processing tasks may be distributed over one or more computing devices in addition to the server computer 204, including the client computer 206 and/or other networked computing devices.

In some cases, the client computer 206 may be configured to control the robot testing apparatus 202. The display 240 may thus be used to provide a user interface for an operator of the robot testing apparatus 202. The user interface may be integrated with the visualization interface to any desired extent.

Figure 3:
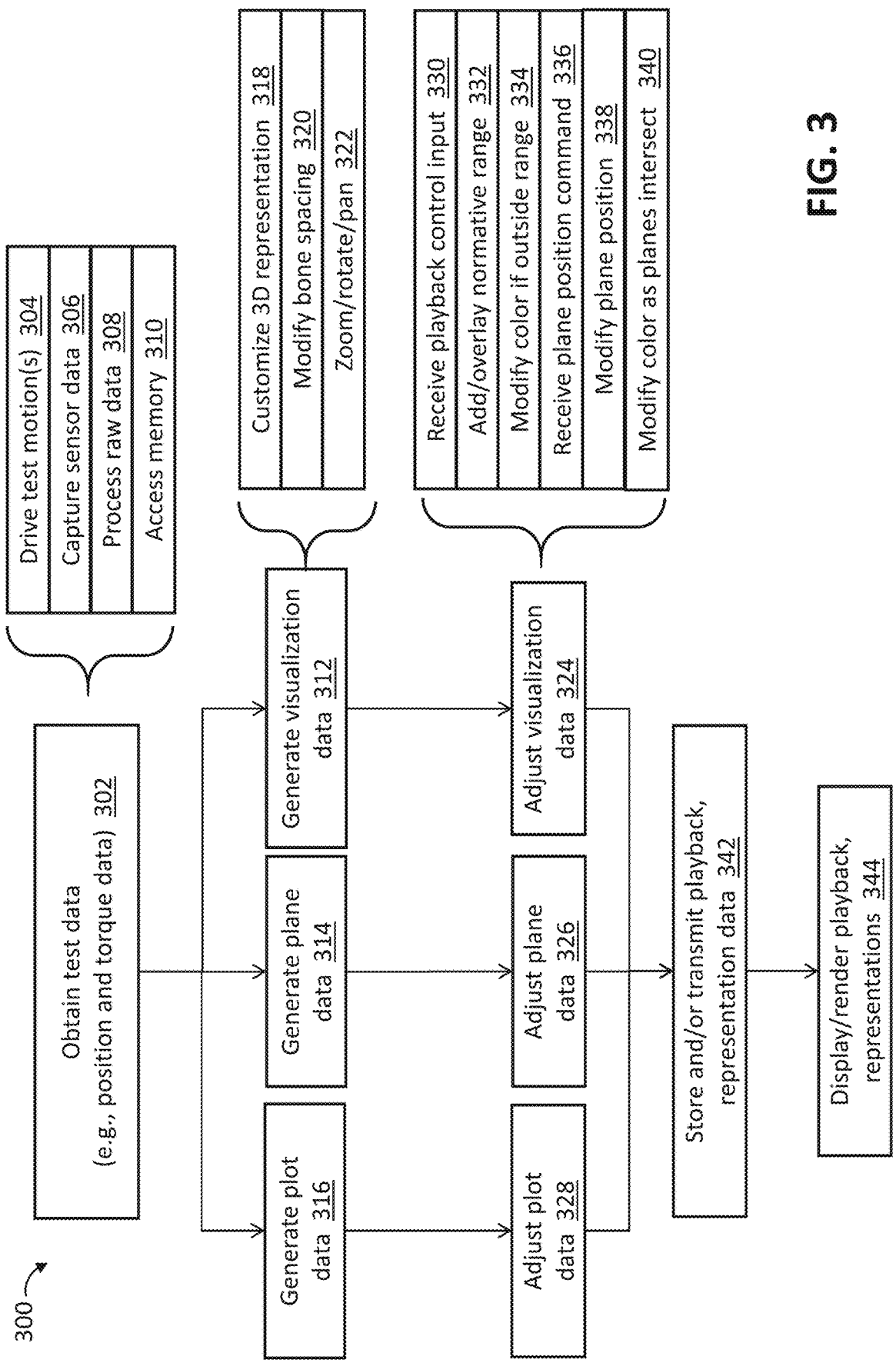
FIG. 3 is a flow diagram of a method for evaluation of joint test data in accordance with one example.

FIG. 3 depicts a method 300 of evaluating knees and other joints. The method 300 is computer-implemented. The method 300 may be implemented by the system 200 of FIG. 2. In some cases, for instance, the processor 220 (FIG. 2) implements one or more acts of the method 300. Alternatively or additionally, the processor 214 (FIG. 2) of the robot testing apparatus 202 and/or the processor 236 (FIG. 2) implements one or more acts of the method 300. In these cases, the processor 220 and/or another processor are configured via execution of computer-readable instructions, such as the instructions described above in connection with the system 200, to cause the processor 220 to implement the method 300. The method 300 may be implemented in additional and/or alternative ways. For instance, one or more acts of the method 300 may be implemented by a remote processor, such as a processor in communication with the processor 220 and/or the processor 236.

The method 300 includes an act 302 in which test data for a joint under test is obtained. The test data is representative of the response of the joint to forces (e.g., torques) applied or imparted in one or more rotational or translational tests. The joint testing is implemented by a robotic testing apparatus applied to the joint, such as the apparatus described above. The robotic test apparatus may be configured to apply or impart a range of forces to the joint and utilize sensors to gather the test data. The sensors may include position sensors and torque sensors. The test data may accordingly include position data and torque data. Additional or alternative types of data may be acquired. For instance, the data may be indicative of a displacement for a given force or torque level. In cases in which the joint is a knee, the rotational movement may be or include varus-valgus rotational movement of the knee and/or external-internal rotational movement of the knee.

The forces are applied or imparted during each joint test in one or more degrees of freedom. Each applied or imparted force in each joint test may be oriented in a respective plane. As described above, each joint test may be characterized by referring to these degree(s) of freedom and plane(s) as primary degree(s) of freedom and primary plane(s) for the joint test. The movement that arises from the applied or imparted forces in the other degrees of freedom may be characterized as secondary or concomitant movement.

The manner in which the test data is obtained may vary. The act 302 may include an act 304 in which one or more joint test(s) motions are driven by the robotic test apparatus. Sensor data may then be captured in an act 306. As described above, obtaining the test data may include the processing of the raw sensor data in an act 308. The processing may be directed to determine position data and generate load-deformation curves from the position data. The data processing may include a number of additional (e.g., subsidiary) processing steps. For instance, the raw sensor data may be processed via one or more coordinate system transformations and interpolation. In other cases, the raw sensor data has already been captured, processed, and/or otherwise obtained, in which case the load-deformation data is obtained by accessing a memory in an act 310.

After the test data is obtained, visualization data is generated in an act 312 for a three-dimensional representation of the joint to be rendered via a display. Additional data is generated for display along with the three-dimensional representation. The additional data may be concurrently generated with the visualization data. In some cases, the additional data is plot data generated in an act 314 for a graphical representation of the test data to be rendered via the display. The graphical representation includes a plot and an indicator disposed at a position along the plot. Alternatively or additionally, plane data is generated in an act 316 for a representation of a plane to be rendered via the display with the three-dimensional representation of the joint, the plane having a position and an orientation fixed relative to a bone of the joint.

The generation of the visualization and additional data may involve various types of customization of the representation(s) rendered via the display. In the example of FIG. 3, the customization of the three-dimensional representation is implemented in an act 318. The customization may include or involve, for instance, selecting one or more views or perspectives to be represented. Alternatively or additionally, the customization may involve modifying, in an act 320, a bone gap or other spacing of the three-dimensional representation. The three-dimensional representation may be customized in still other ways, including, for instance, changing a zoom level, rotating and/or panning the view in an act 322. User inputs to these ends may be received via the user interface by which the representations are rendered. Still further types of customization may be implemented, including, for instance, customization of the plane data and/or the plot data. For example, the customization may involve selecting the respective plots to be rendered.

The method 200 then includes a number of acts directed to playback of the joint movement. The playback may involve animation of the three-dimensional and graphical representations. The animation of the three-dimensional representation is implemented in an act 324 in which the visualization data is adjusted. The adjustment updates the three-dimensional representation to depict, via the display, a playback of the movement of the joint during the test. The plane data is adjusted in an act 326 to update the position and the orientation of the plane(s) in accordance with the movement of the joint. The plot data is adjusted in an act 328 to update the position of the indicator during the playback such that the position of the indicator is representative of a current position of the joint (e.g., the mobile bone of the joint) as depicted via the three-dimensional representation.

The adjustments may be triggered by a user input or command to initiate playback received in an act 330. For instance, the user interface may include a play/pause button for user selection.

The adjustments may include modifications of the three-dimensional and graphical representations in addition to position. For example, the visualization, plane, and/or plot data may be adjusted in an act 332 to add, overlay, or otherwise reflect a normative range of the joint movement. The color and/or other characteristics of the planes and/or depicted elements of, e.g., the three-dimensional representation, may then be modified in an act 334 to indicate when the test data is outside of the normative range or other data, such as a threshold for speed of the movement. The speed of the moving bone exceeding a threshold may be indicate slippage of the bone. Other adjustments may be initiated by user inputs or commands, including, for instance, a plane positioning command received in an act 336 to adjust the position of a plane. The plane position may then be modified accordingly in an act 338. Yet another type of adjustment implemented during playback may involve modifying in an act 340 the color or other characteristic of the plane(s) as the planes intersect.

In some cases, the above-described adjustments to the visualization, plane, and plot data are implemented as a whole for the entire playback sequence. The resulting playback dataset may then be stored and/or transmitted in an act 342. For example, the dataset may be transmitted to a client computer. The playback may then be displayed or rendered on a display of the client computer in an act 344. In some cases, a depiction of normative motion of the joint may be rendered while, before, or after the rendering of the playback, e.g., of the three-dimensional representation of the test data. For example, the normative motion of the joint may be displayed in a semi-transparent manner to allow the playback of the test data to be rendered simultaneously therewith.

The above-described methods described herein may vary from the examples shown.

For instance, one or more of the acts may be performed as described but in a different order. Specific steps may be eliminated or altered and additional steps may be added.

The above-described systems and methods may provide viewer or visualization functionality having one or more of the following features, examples of which are shown in FIGS. 4 and 5.

- Visualization of standard or default bones (e.g., tibia/fibula and femur)
- Visualization of bones undergoing three-dimensional movement defined from the test data generated via robotic apparatus testing.
- User interface buttons or other controls to control the motion playback.
- User interface buttons or other controls to select the test data from a specific test (e.g., anterior-posterior translation, internal-external rotation, varus-valgus rotation).
- Once a test is selected, user interface controls to play the motion in either direction (e.g., anterior or posterior) or to play a loop of the entire test.
- Selective incorporation of planes on the end of the bones that help to accentuate the small motions of the bone such that understanding of the bone movement without having to resort to exaggeration of the motion.
- Customized positioning of the planes to different spots on the bones.
- Multiple standard or default views for each test. The default views were selected based on the views that would most likely show abnormal motion during that specific test. For the AP test, the default views are a side view looking from between the knees towards the lateral side in the large window (main view) and the 180 degree opposite side view and a view looking from the upper leg down towards the foot in the two side views.
- User interface buttons or controls to set a view as a default view. The views are adjustable because different surgeons may focus on different views.
- Depiction of multiple graphical views of the test data. Default graphical views may be provided based on the specific test, and can be changed by individual users. The graphs may show the data for the left and right knees on the same graph.
- A colored ball, dot, or other indicator on the graph that moves along the data line to correlate the motion of the bones to the position on the data graphs.
- User interface button or control to allow a user to switch which leg is the focus of the viewer. This will affect the camera views and which of the graph lines the ball moves along.
- User interface slide bars or other controls to manipulate (e.g., rotate and/or zoom) the three-dimensional representation while the motion is being depicted.

A number of user settings provide options for the visualization. The user settings may be provided in a pulldown tab or other panel or window. An example of a user settings panel is depicted in FIG. 6. Examples of options include—

- Turn individual bones on/off;
- Turn planes on/off;
- Adjust the offset of the planes;
- Adjust the transparency of the planes;
- Adjust the joint space;
- Turn axis on/off;
- Turn grid on/off;
- Turn floor on/off;
- Change camera views;
- Turn on example healthy knee data;
- Run a test of the visualization environment.

The systems and methods described above may be used in conjunction with a manual method of testing.

Each processor 220, 236 may be or include any number or type of processing cores, processors, processing units (e.g., a central processing unit or graphical processing unit), or processing systems. Each processor 220, 236 may be a component in a variety of systems. For example, each processor 220, 236 may be part of a standard personal computer or a workstation. Each processor 220, 236 may be or include one or more general processors, digital signal processors, application specific integrated circuits, field programmable gate arrays, servers, networks, digital circuits, analog circuits, combinations thereof, or other now known or later developed devices for analyzing and processing data.

Each memory 222, 238 may be or include any number or type of computer-readable memories, media, or other devices on which data is stored. Each memory 222, 238 may be or include a main memory, a static memory, or a dynamic memory. Each memory 222, 238 may include, but may not be limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one case, each memory 222, 238 may include a cache or random access memory for a processor. Alternatively or additionally, each memory 222, 238 may be separate from the processor, such as a cache memory of a processor, the system memory, or other memory. Each memory 222, 238 may be or include an external storage device or database for storing data. Examples may include a hard drive, compact disc ("CD"), digital video disc ("DVD"), memory card, memory stick, floppy disc, universal serial bus ("USB") memory device, or any other device operative to store data. Each memory 222, 238 may be operable to store instructions executable by a processor. The functions, acts or tasks illustrated in the figures or described herein may be performed by the programmed processor executing the instructions stored in the memory 222, 238. The functions, acts or tasks may be independent of the particular type of instruction set, storage media, processor or processing strategy and may be performed by software, hardware, integrated circuits, firmware, micro-code and the like, operating alone or in combination. Likewise, processing strategies may include multiprocessing, multitasking, parallel processing and the like.

The present disclosure has been described with reference to specific examples that are intended to be illustrative only and not to be limiting of the disclosure. Changes, additions and/or deletions may be made to the examples without departing from the spirit and scope of the disclosure.

The foregoing description is given for clearness of understanding only, and no unnecessary limitations should be understood therefrom.

What is claimed is:

1. A method of evaluating a joint, the method comprising:
    obtaining, by a processor, test data indicative of movement of the joint during a test of the joint;

generating, by the processor, visualization data for a three-dimensional representation of the joint to be rendered via a display;

generating, by the processor, plane data for a representation of a plane to be rendered via the display with the three-dimensional representation of the joint, the plane having a position and an orientation fixed relative to a bone of the joint;

adjusting, by the processor, the visualization data to animate the three-dimensional representation to depict, via the display, the movement of the joint during the test; and adjusting, by the processor, the plane data to update the position and the orientation of the plane in accordance with the movement of the joint.

2. The method of claim 1, wherein adjusting the plane data modifies a characteristic of the plane when the movement falls outside of a normative range of motion for the joint.

3. The method of claim 1, further comprising adjusting, by the processor in response to a user input, the plane data to change the position of the plane relative to the bone.

4. The method of claim 1, wherein the plane is a first plane of a plurality of planes, the method further comprising:

generating, by the processor, further plane data for a representation of a second plane of the plurality of planes, the second plane having a position and an orientation fixed relative to a second bone of the joint; and modifying, by the processor, a characteristic of the second plane when the first plane and the second plane intersect.

5. The method of claim 4, wherein the second bone is a stationary bone during the test.

6. The method of claim 1, further comprising modifying, by the processor, a characteristic of the three-dimensional representation when the movement falls outside of a normative range of motion for the joint.

7. The method of claim 1, wherein generating the three-dimensional representation comprises customizing the three-dimensional representation to modify a bone spacing of the joint.

8. The method of claim 1, wherein generating the three-dimensional representation of the joint comprises:

receiving a user input directed to modification of the three-dimensional representation; and modifying a zoom level and/or a viewing perspective of the three-dimensional representation in response to the user input.

9. The method of claim 1, wherein adjusting the three-dimensional representation comprises receiving a user input directed to controlling playback of the movement of the joint during the test.

10. The method of claim 1, wherein adjusting the three-dimensional representation comprises depicting the movement in scale relative to dimensions of the joint.

11. The method of claim 1, wherein obtaining the test data comprises capturing the test data via a robotic test apparatus.

12. The method of claim 1, further comprising rendering, by the processor, on the display, the adjusted three-dimensional representation of the joint and the representation of the plane with the updated position and the updated orientation of the plane to depict the movement of the joint.

13. The method of claim 12, further comprising rendering, by the processor, on the display, a depiction of normative motion of the joint while rendering the three-dimensional representation of the test data.

14. A method of evaluating a joint, the method comprising:

obtaining, by a processor, test data indicative of movement of a mobile bone of the joint relative to a stationary bone of the joint during a test of the joint in which the mobile bone moves relative to the stationary bone;

generating, by the processor, visualization data for a three-dimensional representation of the joint to be rendered via a display;

generating, by the processor, plot data for a graphical representation of the test data to be rendered via the display, the graphical representation comprising a plot and an indicator disposed at a position along the plot;

adjusting, by the processor, the visualization data to update the three-dimensional representation to depict, via the display, a playback of the movement of the mobile bone relative to the stationary bone during the test; and adjusting, by the processor, the plot data to update the position of the indicator during the playback such that the position of the indicator is representative of a current position of the mobile bone as depicted via the three-dimensional representation.

15. The method of claim 14, further comprising:

generating, by the processor, plane data for a representation of a plane to be rendered via the display with the three-dimensional representation of the joint, the plane having a position and an orientation fixed relative to the mobile bone of the joint; and adjusting, by the processor, the plane data to update the position and the orientation of the plane in accordance with the movement of the joint.

16. The method of claim 15, wherein adjusting the plane data modifies a characteristic of the plane when the movement falls outside of a normative range of motion for the joint.

17. The method of claim 15, further comprising adjusting, by the processor in response to a user input, the plane data to change the position of the plane relative to the bone.

18. The method of claim 15, wherein the plane is a first plane of a plurality of planes, the method further comprising:

generating, by the processor, further plane data for a representation of a second plane of the plurality of planes, the second plane having a position and an orientation fixed relative to a stationary bone of the joint; and modifying, by the processor, a characteristic of the second plane when the first plane and the second plane intersect.

19. The method of claim 14, wherein the graphical representation comprises a load-deformation curve.

20. The method of claim 14, wherein the graphical representation depicts the movement in a secondary degree of freedom other than a primary degree of freedom in which a force is applied to the joint to cause the movement.

21. The method of claim 14, further comprising adding, by the processor, a depiction of normative motion of the joint to the graphical representation of the test data.

22. A system for evaluation of a joint, the system comprising:

a memory in which modeling instructions and data processing instructions are stored; and a processor coupled to the memory and configured through execution of the data processing instructions to obtain test data for a joint, the test data being indicative of movement of a mobile bone of the joint relative to a stationary bone of the joint during a test of the joint in which the mobile bone moves relative to the stationary bone;

wherein the processor is configured through execution of the modeling instructions to generate visualization data for a three-dimensional representation of the joint to be rendered via a display;

wherein the processor is further configured through the execution of the modeling instructions to generate plane data for a representation of a plane to be rendered via the display with the three-dimensional representation of the joint, the plane having a position and an orientation fixed relative to the mobile bone of the joint;

wherein the processor is further configured through the execution of the modeling instructions to adjust the visualization data to update the three-dimensional representation to depict, via the display, a playback of the movement of the mobile bone relative to the stationary bone during the test; and wherein the processor is further configured through the execution of the modeling instructions to adjust the plane data to update the representation of the plane in accordance with the movement of the joint.

23. The system of claim 22, wherein:

graphical plot instructions are stored in the memory;

the processor is configured through execution of the graphical plot instructions to generate plot data for a graphical representation of the test data to be rendered via the display, the graphical representation comprising a plot and an indicator disposed at a position along the plot; and the processor is further configured through the execution of the graphical plot instructions to adjust the plot data to update the position of the indicator during the playback such that the position of the indicator is representative of a current position of the mobile bone as depicted via the three-dimensional representation.

\* \* \* \* \*